United States Patent
Kokke et al.

(10) Patent No.: US 9,845,338 B2
(45) Date of Patent: Dec. 19, 2017

(54) METHOD OF PURIFYING AN ANTIBODY

(75) Inventors: Bastiaan Pieter Arjan Kokke, Nijmegen (NL); Everdina Josephina Wilhelmina Wijk-Basten Van, Nijmegen (NL); Thomas Antonius Bernardus Beijer De, Nijmegen (NL); Maria Marzá Pérez, Nijmegen (NL); Michel Hendrikus Maria Eppink, Nijmegen (NL)

(73) Assignee: Synthon Biopharmaceuticals BV, Nijmegen (NL)

(*) Notice: Subject to any disclaimer, the term of this patent is extended or adjusted under 35 U.S.C. 154(b) by 284 days.

(21) Appl. No.: 14/410,562

(22) PCT Filed: Jun. 21, 2012

(86) PCT No.: PCT/EP2012/062014
§ 371 (c)(1),
(2), (4) Date: Sep. 16, 2015

(87) PCT Pub. No.: WO2013/189544
PCT Pub. Date: Dec. 27, 2013

(65) Prior Publication Data
US 2016/0002289 A1    Jan. 7, 2016

(51) Int. Cl.
*C07K 1/36* (2006.01)
*C07K 16/06* (2006.01)
*C07K 16/32* (2006.01)
*C07K 1/34* (2006.01)
*C07K 1/18* (2006.01)

(52) U.S. Cl.
CPC .............. *C07K 1/36* (2013.01); *C07K 16/065* (2013.01); *C07K 16/32* (2013.01); *C07K 1/18* (2013.01); *C07K 1/34* (2013.01); *C07K 2317/14* (2013.01)

(58) Field of Classification Search
None
See application file for complete search history.

(56) References Cited

U.S. PATENT DOCUMENTS

| | | | | |
|---|---|---|---|---|
| 2003/0118583 A1* | 6/2003 | Emery | ............. | A61K 39/39591 424/130.1 |
| 2007/0292442 A1* | 12/2007 | Wan | ......................... | C07K 1/18 424/176.1 |
| 2009/0017017 A1* | 1/2009 | Rasmussen | .......... | C07K 16/005 424/133.1 |
| 2010/0150864 A1* | 6/2010 | Hickman | ............. | C07K 16/244 424/85.2 |
| 2012/0135007 A1* | 5/2012 | Ilan | .................. | A61K 39/39508 424/172.1 |
| 2012/0237526 A1* | 9/2012 | De Strooper | .......... | C07K 16/40 424/158.1 |
| 2016/0264617 A1* | 9/2016 | Dong | ............... | A61K 39/39591 |

FOREIGN PATENT DOCUMENTS

| | | | | |
|---|---|---|---|---|
| WO | WO 2005082937 A2 * | 9/2005 | ............ | A61L 2/0011 |
| WO | WO 2009085765 A1 * | 7/2009 | .......... | C07K 16/065 |
| WO | WO 2011/012637 A2 | 2/2011 | | |
| WO | WO 2011/015920 A2 | 2/2011 | | |
| WO | WO 2012/013682 A2 | 2/2012 | | |
| WO | WO 2012013682 A2 * | 2/2012 | ............... | C07K 1/18 |

OTHER PUBLICATIONS

Baselga, J., et al., "Phase II Trial of Pertuzumab and Trastuzumab in Patients With Human Epidermal Growth Factor Receptor 2—Positive Metastatic Breast Cancer That Progressed During Prior Trastuzumab Therapy," *Journal of Clinical Oncology.* 28(7):1138-1144, American Society of Clinical Oncology, United States (2010).

Gagnon, P., "Technology Trends in Antibody Purification," *Journal of Chromatography A 1221*:57-70, Elsevier B.V., The Netherlands (available online Oct. 20, 2011).

Liu, H.F., et al., "Recovery and Purification Process Development For Monoclonal Antibody Production," *mAbs* 2(5):480-499, Landes Bioscience, United States (2010).

International Search Report for International Application No. PCT/EP2012/062014, European Patent Office, Rijswijk, The Netherlands, dated Mar. 6, 2013, 4 pages.

International Preliminary Examination Report and Written Opinion for International Application No. PCT/EP2012/062014, WIPO, Geneva, Switzerland, dated Dec. 23, 2014, 7 pages.

\* cited by examiner

*Primary Examiner* — Daniel E Kolker
*Assistant Examiner* — James Rogers
(74) *Attorney, Agent, or Firm* — Sterne, Kessler, Goldstein & Fox P.L.L.C.

(57) ABSTRACT

A method of purifying an antibody composition comprises application of anion exchange chromatography late in the purification process. An ultrafiltration/diafiltration-purified antibody composition is subjected to anion exchange chromatography (AEX) to form a pharmaceutically-pure antibody composition.

22 Claims, No Drawings

METHOD OF PURIFYING AN ANTIBODY

FIELD OF THE INVENTION

The present invention relates to methods of purifying an antibody. In particular, the methods involve the late-stage use of anion exchange chromatography in an antibody purification process.

BACKGROUND OF THE INVENTION

Monoclonal antibodies (mAbs) are one of the most important agents in the pharmaceutical industry. mAbs typically are produced using cultured cells, with mammalian cells often being used to ensure desired folding and glycosylation. Over the last decade, advances have been made in cell culture technology, including the improvement of production media and feeding strategies. These advances have resulted in high cell culture titers. The expressed antibodies, however, generally need to be separated from the host cells and the other components (impurities) in the expression medium in order to be used for their intended purposes.

Because mAbs are generally produced by fermentation, they are accompanied by large amounts of process-related impurities such as host cell protein (HCP), host cell DNA, and media components. Mammalian cells, for example, are sensitive to breakage due to shear stress, and this can result in the release of impurities, such as proteases (i.e., an HCP), which can affect product stability and/or purity. HCP in particular is an important contaminant because it can provoke an immune response at the low parts per million level. Depending on the fermentation conditions, product-related impurities, such as degraded, truncated, and aggregated mAbs, may also be found in the cell culture supernatant. The efficient recovery and purification of antibodies from cell culture media is thus an important part of the antibody purification process, especially in pharmaceutical applications.

Current mAb purification processes generally contain chromatographic polishing steps that target the reduction/removal of product-related and process-related impurities, such as HCP and DNA, high-molecular weight (MW) aggregates, low-MW degradation products, and leachables. Purification processes can be broken down into a series of unit operations, although the operations (and steps therein) can occur simultaneously or sequentially. A common Protein A-based antibody purification process, which covers a broad range of antibodies and conditions, comprises the following unit operations: Protein A capture low→pH virus inactivation→ion exchange chromatography (IEX) polishing (typically two ion exchange chromatography followed by anion exchange chromatography)→virus filtration→and a final ultrafiltration-diafiltration (UF/DF). Further details of antibody purification techniques can be found in Process Scale Purification of Antibodies, Edited by Uwe Gottschalk, John Wiley & Sons, Inc. 2009. The final UF/DF step is considered to complete the purification and to place the antibody into a composition suitable for end-use applications, such as bulk fill and finish, lyophilization for pharmaceutical applications, in vivo testing, clinical use, etc.

Accordingly, it would be desirable to provide an alternative purification process for purifying an antibody composition.

BRIEF SUMMARY OF THE INVENTION

The present invention is based on the discoveries that conventional antibody purification processes are not as effective as previously believed, especially regarding HCP, and that the use of anion exchange chromatography (AEX) late in the purification process can improve the purification process and/or provide higher quality antibody compositions. Accordingly, a first aspect of the invention relates to a method of purifying an antibody composition, which comprises subjecting a UF/DF-purified antibody composition to anion exchange chromatography (AEX) to form a pharmaceutically pure antibody composition. "Pharmaceutically pure" in this context is defined hereinafter. The UF/DF-purified antibody composition typically has an antibody concentration of at least 1 mg/ml, such as at least 5 mg/ml, at least 10 mg/ml, 5 to 250 mg/ml, 10 to 150 mg/ml, 15 to 100 mg/ml, 20 to 50 mg/ml, and 30-35 mg/ml. The UF/DF-purified antibody composition is typically obtained by subjecting a partially-purified antibody composition to UF/DF. The partially-purified antibody composition can be formed by a capture and/or polishing step(s).

Another aspect of the invention relates to a method of purifying an antibody composition, which comprises: subjecting an antibody cell culture harvest to affinity chromatography, such as Protein A chromatography, to capture a crude antibody composition; subjecting the crude antibody composition to at least one polishing step to form a partially-purified antibody composition; subjecting the partially-purified antibody composition to a UF/DF step to form a UF/DF-purified antibody composition; and subjecting the UF/DF-purified antibody composition to anion exchange chromatography (AEX) to form a pharmaceutically pure antibody composition. The polishing step is often cation exchange chromatography and optionally followed by anion exchange chromatography.

A further aspect of the invention relates to a method of purifying an antibody composition, which comprises subjecting an antibody composition having an antibody concentration of at least 1 mg/ml, such as at least 5 mg/ml, at least 10 mg/ml, 5 to 250 mg/ml, 10 to 150 mg/ml, 15 to 100 mg/ml, 20 to 50 mg/ml, and 30-35 mg/ml, and having a parenterally-acceptable buffer and pH, to anion exchange chromatography (AEX) sufficient to reduce the amount of host cell proteins in said antibody composition.

DETAILED DESCRIPTION OF THE INVENTION

The present invention relates to a method of purifying an antibody using AEX late in the purification, relative to the previously known purification techniques. Conventional mAb purification processes, which use a capture step followed by IEX polishing steps and ending on a final UF/DF step before bulk filling, were thought to be proficient in achieving desirably-low levels of HCP. Common ELISA-based HCP detection kits often showed suitably low amounts of HCP after the final UF/DF step. But after switching to a newer, more sensitive ELISA-based HCP detection kit, the present inventors discovered that the amount of HCP was actually much higher than previously thought and beyond the desired purity limit. Based on this discovery, the inventors sought to find a purification process that would provide a higher purity antibody composition.

The inventors found that AEX can be performed after the final UF/DF step with improved purification effects. As shown in the Examples below, moving AEX from the pre-UF/DF polishing stage to post-UF/DF provided superior HCP removal without any unwanted rise in other measured impurities. Locating the AEX step after UF/DF increased the purification effect as compared to conventional processes.

Performing AEX after the final ultrafiltration is also advantageous from an economical and/or time perspective. The AEX step can generally be performed faster after UF/DF than before (i.e., during the polishing phase) because the antibody composition is more concentrated after the final UF/DF (e.g. less volume). Another benefit of the invention is enhanced virus control; AEX is known to remove some viruses. When AEX is performed in as a polishing step (pre-UF/DF), subsequent processes and handling risk re-introduction of viruses. That risk can be minimized by performing AEX later in the purification scheme.

In one embodiment, a UF/DF-purified antibody composition is subjected to AEX. A "UF/DF-purified antibody composition" is one that has undergone some level of purification and has undergone a UF/DF step. In the typical prior art purification process described above, the final UF/DF step produces a UF/DF-purified antibody composition. The composition need not be, and typically is not, completely or sufficiently pure. Rather, some level of impurity removal has been performed and some concentrating of the antibody composition via UF/DF has happened. This distinguishes the UF/DF-purified antibody composition as used in the present invention from an antibody composition that has been subjected to UF/DF prior to capture; e.g., as part of a clarifying or preparatory step to facilitate the capture step, at least because such clarifying or preparatory steps result in a composition of insufficiently low concentration that is not suitable for end use. Such an antibody composition is also typically of low concentration.

The UF/DF-purified antibody composition of the present invention typically has an antibody concentration of at least 1 mg/ml, more typically at least 5 mg/ml, preferably at least 10 mg/ml, including at least 15 mg/ml. For practical reasons, the antibody concentration is typically not greater than 250 mg/ml. Accordingly, the antibody concentration is typically in the range of 5 to 150 mg/ml. In some embodiments, the concentration is in the range of 10 to 65 mg/ml including 15 to 50 mg/ml, such as 30 to 35 mg/ml. In other embodiments, the antibody concentration is in the range of 50 to 150 mg/ml, including 75 to 100 mg/ml.

In some embodiments, the UF/DF-purified antibody composition of the present invention contains the antibody in a parenterally-acceptable buffer and pH. Typically the antibody concentration is at least 10 mg/ml in such an embodiment and includes the ranges mentioned above, e.g., 15 to 50 mg/ml, such as 30 to 35 mg/ml. Conventionally, the treatment of an antibody composition in near final form (e.g., having a buffer medium suitable for pharmaceutical injection) with a chromatography step for further purification was counter-intuitive. The UF/DF step was considered the final step and placed the purified antibody composition into the appropriate concentration and buffer. Further purification steps post-UF/DF were considered to be disadvantageous, e.g., because of the high cost associated with late-stage lost yield and/or because of the risk of introducing leachables and/or extractables late in the purification process.

A parenterally-acceptable buffer is an aqueous composition, typically containing acetate, phosphate, histidine, and/or citrate buffer, in amounts suitable for parenteral administration, typically 1-50 millimolar. The pH of the composition is likewise consistent with parenteral formulations and administration and is typically within the range of pH 4 to 8, preferably pH 6 to 8. Conversely, the parenterally-acceptable buffer does not contain dangerous or parenterally-unacceptable amounts of prior purification reagents. In some embodiments, the parenterally-acceptable buffer composition further comprises a surfactant and/or a stabilizer for the antibody.

Per the present invention, the UF/DF-purified antibody composition is subjected to AEX. For clarity, anion exchange chromatography or "AEX" refers to a method by which a composition comprising an antibody and one or more impurities (e.g., process-related impurities, such as host-cell proteins, DNA, and/or endogenous or adventitious viruses (e.g., MulV or MVM)) can be separated based on charge differences using an anion exchange matrix. An anion exchange matrix generally comprises covalently bound, positively charged groups. Strong or weak anion exchange matrices can be employed. Examples of strong anion exchange matrices include those having a quaternary ammonium ion. Examples of weak anion exchange matrices include those having either a tertiary or secondary amine functional group, such as DEAE (diethylaminoethyl). In certain embodiments, multimodal anion exchange matrices can be used, which incorporate additional binding mechanisms as well as the ionic interactions, for example one or more of hydrogen bonding interactions and hydrophobic interactions. Examples of suitable anion exchange matrices are known in the art, and can include, but are not limited to, Sartobind Q, Natrix Q, Chromasorb Q, and Mustang Q. Mustang Q is a preferred anion exchange matrix.

The anion exchange chromatography process can be employed in either binding mode or flow-through mode with respect to the antibody, as is well known in the art. In binding mode, the antibody of interest is adsorbed to the anion exchange matrix, while one or more impurities do not bind, thus separating the antibody from the impurity. In some embodiments, the anion exchange matrix is washed one or more times with a buffer to remove additional impurities before the adsorbed antibody is removed from the anion exchange matrix. After one or more impurities have been removed from a composition employing anion exchange chromatography in binding mode, the adsorbed antibody can be removed (eluted) from the anion exchange matrix. In contrast, flow-through mode means that the antibody of interest is not significantly adsorbed to the anion exchange matrix, while one or more impurities is adsorbed (or impeded) to the matrix. The antibody flows through the column while the impurities are bound, thus causing a separation of the impurities from the antibody. Periodically the matrix will need to be rejuvenated by removing the bound impurities or replaced with new matrix material.

In the present invention, the application of AEX has a purifying effect on the antibody composition. Accordingly, a UF/DF-purified antibody composition becomes a pharmaceutically-pure antibody composition after being subjected to AEX according to the invention. A "pharmaceutically-pure antibody composition" as used herein means a composition whose product-related impurities (e.g., antibody fragments, oligomers, etc.) and process-related impurities (e.g., host cell DNA and HCP, etc.) are below pharmaceutically-acceptable levels. Such levels are those generally accepted by workers in the pharmaceutical field for a composition that is to be administered to a human or animal. For an approved antibody product, the standard adopted by the U.S. FDA or the EMA of Europe for limiting such impurities can define the upper limit of pharmaceutically-pure (if different limits between US and EU, whichever is higher). In general, a pharmaceutically-pure antibody composition requires no further purification from product-related or process-related impurities, but may require sterile filtering or other modifications to form a final dosage form.

In short, the act of purifying is essentially complete. In embodiments, a pharmaceutically-pure antibody composition according to the present invention will typically satisfy the following specifications: (1) HCP concentration of 10 ppm (parts per million) or less, preferably 5 ppm or less, and more preferably 2 ppm or less; and (2) DNA concentration of 20 ppb (parts per billion) or less, preferably 10 ppb or less, more preferably 5 ppb or less, and often less than 1 ppb. If Protein A or other protein reagent is used upstream in the purification process, then it is usually desired that the amount of (leached) Protein A is limited to a concentration of 20 ppm or less, typically 10 ppm or less, often 5 ppm or less, and in some embodiments 1 ppm or less. Also, in some embodiments, a pharmaceutically-pure antibody composition will typically have no more than 5% dimer and aggregates, preferably no more than 2%, and often no more than 1%, based on the total amount of antibody, dimers, and aggregates. The amount of such impurities can also be expressed relative to the amount of the antibody. For instance, the amount of HCP in the pharmaceutically-pure antibody composition is typically less than about 10 ng/mg of antibody, preferably less than about 5 ng/mg, more preferably less than about 2 ng/mg.

Suitable conditions for carrying out the AEX step are generally known in the art and can be determined or optimized using routine skill and procedures. The AEX step as used in the present invention reduces the concentration or amount of at least one impurity. Thus, a UF/DF-purified antibody composition is transformed into a pharmaceutically-pure antibody composition by subjecting it to AEX and thereby reducing at least one impurity. Typically, though not necessarily, the impurity being reduced is HCP. A particular embodiment of the present invention comprises subjecting a UF/DF-purified antibody composition (having a concentration of at least 10 mg/ml and parenterally acceptable buffer and pH) to AEX in order to reduce the concentration or amount of HCP. In all embodiments, the degree of reduction is not particularly limited and includes small but detectable purity improvements; such as from 25 ppm to 20 ppm to thereby meet a purity specification, etc. Typically, however, the magnitude of purity enhancement is more significant.

Antibodies that can be purified in the present invention are not particularly limited. For clarity, an "antibody" is taken in its broadest sense and includes any immunoglobulin (Ig), active or desired variants thereof, and active or desirable fragments thereof (e.g., Fab fragments, camelid antibodies (single chain antibodies), and nanobodies). The antibody can be polyclonal or monoclonal and can be naturally-occurring or recombinantly-produced. Thus, human, non-human, humanized, and chimeric antibodies are all included with the term "antibody." Typically the antibody to be purified in the process of the invention is a monoclonal antibody of one of the following classes: IgG, IgE, IgM, IgD, and IgA; and more typically is an IgG or IgA. The antibody can be directed against a variety of antigens, as is well known in the art, including but not limited to a cancer-related antigen (e.g., HER-2) or a pro-inflammatory antigen (e.g., a pro-inflammatory cytokine, such as TNF-α). Examples of suitable anti-inflammatory antibodies include, but are not limited to, anti-TNFalpha antibodies such as adalimumab, infliximab, etanercept, golimumab, and certolizumab pegol; anti-IL1beta antibodies such as canakinumab; anti-IL12/23 (p40) antibodies such as ustekinumab and briakinumab; and anti-IL2R antibodies, such as daclizumab. Examples of suitable anti-cancer antibodies include, but are not limited to, anti-BAFF antibodies such as belimumab; anti-CD20 antibodies such as rituximab; anti-CD22 antibodies such as epratuzumab; anti-CD25 antibodies such as daclizumab; anti-CD30 antibodies such as iratumumab, anti-CD33 antibodies such as gemtuzumab, anti-CD52 antibodies such as alemtuzumab; anti-CD152 antibodies such as ipilimumab; anti-EGFR antibodies such as cetuximab; anti-HER2 antibodies such as trastuzumab and pertuzumab; anti-IL6 antibodies such as siltuximab; and anti-VEGF antibodies such as bevacizumab.

Antibodies are routinely produced or expressed in cells in a culture medium. The cells can be bacteria, plant, or mammalian cells as is well known in the art. In one embodiment of the invention, the antibody is produced in eukaryotic cells, e.g., mammalian cells. One of skill in the art can select an appropriate cell line depending on the particulars of antibody of interest. Suitable mammalian cells include, e.g., CHO, VERO, BHK, HeLa, CV1, MDCK, 293, 3T3, C127, PC12, HEK-293, PER C6, Sp2/0, NSO, W138 cells and myeloma cell lines (especially murine). Mammalian cells derived from any of the foregoing cells may also be used. In one embodiment of the invention, the antibody is produced by CHO cells.

The culturing medium in which the cells produce the antibodies is generally well known and can be determined by a worker of skill in the art. Typically, the medium is designed based on the specific needs of the host cell and the clone, as is well known in the art. The medium can contain a variety of ingredients such as inorganic salts, carbohydrates (e.g., sugars such as glucose, galactose, maltose or fructose) amino acids, vitamins (e.g., B group vitamins (e.g., B 12), vitamin A vitamin E, riboflavin, thiamine and biotin), fatty acids and lipids (e.g., cholesterol and steroids), proteins and peptides or dipeptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, copper, selenium and tricarboxylic acid intermediates) and combinations thereof. The medium frequently contains a buffer and common buffers found include PBS, Hanks BSS, Earles salts, DPBS, HBSS, EBSS. Other components found in culturing media can include ascorbate, citrate, cysteine/cystine, glutamine, folic acid, glutathione, linoleic acid, linolenic acid, lipoic acid, oleic acid, palmitic acid, pyridoxal/pyridoxine, riboflavin, selenium, thiamine, transferrin. Culturing media are commercially available from, e.g., Sigma-Aldrich Corporation (St. Louis, Mo.), HyClone (Logan, Utah), Invitrogen Corporation (Carlsbad, Calif.), Cambrex Corporation (E. Rutherford, N.J.), JRH Biosciences (Lenexa, Kans.), Irvine Scientific (Santa Ana, Calif.), and others.

The production of antibodies typically results in the presence of large amounts of unwanted material. For example, process-related impurities such as HCP, nucleic acid (e.g., chromosomal or extrachromosomal DNA; ribonucleic acid (t-RNA or mRNA)) and lipids (e.g., cell wall material) are examples of unwanted materials (cellular debris) from the antibody-producing cells (also known as "host cell"). In addition, media components such as other buffers, media additives, or microbial contaminants (e.g., bacteria and/or virus) are also unwanted materials that should be separated from the intended antibody. Product-related impurities such as multimers (e.g., dimer, trimer, etc.), truncated forms, and agglomerated forms (e.g., misfolded or denatured form) of the intended antibody are typically unwanted materials. These unwanted materials in an antibody composition are referred to as impurities. The antibody composition obtained immediately after production (culturing) is generally the least concentrated and has the most impurities. This initial or raw antibody composition is subjected to purification to recover the intended antibody apart from one or more impurities. Usually the purification involves at least a capture step and often at least one polishing step to form a partially-purified antibody composition.

Before the capture step, the raw antibody composition is sometimes clarified by conventional procedures. For convenience, the raw and clarified antibody compositions are collectively referred to herein as the "initial antibody composition," regardless of whether the antibody composition is clarified.

The capture step is well known in the art. The goal is to rapidly isolate, stabilize, and concentrate the antibody. Ideally, critical or deleterious impurities that could adversely affect activity or yield are removed to a high degree. Suitable techniques for carrying out the capture step include various types of chromatography, such as affinity chromatography (AC), hydrophobic interaction (HIC), ion exchange (IEX) (such as cation exchange chromatography (CEX)), hydrophobic charge induction chromatography (HCIC), and mixed mode chromatography. The antibody composition obtained after the capture step is a "partially-purified antibody composition" for purposes of this invention. For convenience in nomenclature, this captured antibody composition is also sometimes referred to as a "crude antibody composition."

The crude antibody composition can be subjected to one or more polishing steps. The goal in polishing is to remove the bulk of the impurities. Suitable techniques for polishing include ion exchange chromatography (IEX), hydrophobic interaction chromatography (HIC), and hydroxyapatitie chromatography.

Though the above techniques are each well known in the art, affinity chromatography (for capture) and IEX (for capture and/or polishing), being two of the preferred techniques, are described in more detail below.

Affinity chromatography refers to a separation method whereby an antibody, by virtue of its specific binding properties, is bound to an affinity ligand for the antibody. The functional affinity ligand can be immobilized on a solid or semi-solid support so that when a composition comprising the antibody is passed over the ligand and the solid support, the antibody having a specific binding affinity to the ligand adsorbs to the ligand, and one or more other impurities are not adsorbed (or are bound at a lower affinity) and are separated from the antibody. Examples of impurities that do not typically bind (or do not bind well) include process-related impurities (e.g., host cell proteins, DNA, medium components) and some product-related impurities (e.g., antibody fragments). In some embodiments, the solid support comprising the ligand is washed one or more times with a buffer to remove additional impurities before the adsorbed antibody is removed from the ligand and the support. After one or more impurities have been removed, the adsorbed antibody can be removed (eluted) from the ligand and the support, resulting in isolation of the antibody from the original composition. Methods of removing the antibody from the ligand and support are dependent on the ligand and are known to those of skill in the art and can include, e.g., changes in environment, e.g., pH, addition or chaotropic agents or denaturants, or addition of commercially available elution buffers. In some embodiments, more than one affinity purification process can be employed on an antibody composition. Various affinity ligands are known. Two of the most common are Protein A and Protein G (and combinations thereof). Immobilized ligands are commercially available. For example, Protein A affinity systems include Mab-Select, MabSelect SuRe, MabSelect Xtra, MabSelect SuRe LX, Sepaharose CL-4B, ProSep vA, ProSep vA Ultra, ProSep vA UltraPlus, and Ceramic HyperD.

Generally the capture step of the present invention uses Protein A affinity chromatography and specifically uses MabSelect SuRe, ProSep vA Ultra, or Poros MabSelect. MabSelect and MabSelect SuRe both use a highly cross-linked agarose matrix. MabSelect SuRe has been developed to better withstand strong alkaline conditions, commonly used in the cleansing of the column. Modification of the Protein A resin prevents unwanted interaction with the variable domains of the antibody. ProSep vA Ultra is a resin based on porous glass beads. It combines a high binding capacity with a high throughput, but also may have disadvantages such as high Protein A leakage and the need for special cleaning agents. Typically the most preferred embodiment of affinity capture comprises MabSelect SuRe.

Ion exchange chromatography includes cation exchange chromatography (CEX) and anion exchange chromatography (AEX). AEX was described above. CEX is similar and is described below. Cation exchange chromatography refers to any method by which an antibody and some impurity or impurities can be separated based on charge differences using a cation exchange matrix. A cation exchange matrix generally comprises covalently bound, negatively charged groups. Weak or strong cation exchange resins may be employed. Commonly, strong cation exchange resins comprise supported organic groups comprising sulphonic acid or sulphonate groups, depending upon the pH. Weak cation exchanger resins commonly comprise supported organic groups comprising carboxylic acid or carboxylate groups, depending upon the pH. In certain embodiments, multi-modal cation exchange resins can be used, which incorporate additional binding mechanisms as well as the ionic interactions, for example one or more of hydrogen bonding interactions and hydrophobic interactions. Examples of suitable cation exchange resins are well known in the art, and can include, but are not limited to Fractogel, carboxymethyl (CM), sulfoethyl(SE), sulfopropyl(SP), phosphate(P) and sulfonate(S), PROPAC WCX-10™ (Dionex), Capto S, S-Sepharose FF, Fractogel EMD SO3M, Toyopearl Megacap II SP 550C, Poros 50 HS, and SP-sepharose matrix. In preferred embodiments, the cation resin is selected from Capto S, S-Sepharose FF, Fractogel EMD SO3M, Toyopearl Megacap II SP 550C, Poros 50 HS, most preferably Poros 50 HS. In some embodiments, more than one cation exchange chromatography process can be employed on the composition.

The cation exchange chromatography process can be employed in either binding mode or flow-through mode with respect to the antibody, as is well known in the art. In binding mode, the antibody of interest is adsorbed to the cation exchange matrix, while one or more impurities do not bind, thus separating the antibody from the impurity. In some embodiments, the cation exchange matrix is washed one or more times with a buffer to remove additional impurities before the adsorbed antibody is removed from the anion exchange matrix. After one or more impurities have been removed from a composition employing cation exchange chromatography in binding mode, the adsorbed antibody can be removed (eluted) from the cation exchange matrix. In contrast, flow-through mode means that the antibody of interest is not significantly adsorbed to the cation exchange matrix, while one or more impurities is adsorbed (or impeded) to the matrix. The antibody flows through the column while the impurities are bound, thus causing a separation of the impurities from the antibody. Periodically the matrix will need to be rejuvenated by removing the bound impurities or replaced with new matrix material.

The antibody composition resulting from either the capture step or the polishing step is considered a partially-purified antibody composition. Typically the partially-purified antibody composition is formed by subjecting the initial antibody composition to affinity chromatography such as Protein A, CEX, or mixed mode chromatography as a capture step followed by at least one polishing step. The polishing step is often an IEX and particularly a CEX step. In some embodiments, the polishing step comprises CEX and AEX in any order (i.e., CEX followed by AEX; AEX followed by CEX). A partially-purified antibody composition, with or without additional treatment(s), is then typically subjected UF/DF to form a UF/DF-purified antibody composition.

In addition to the capture and polishing steps discussed above, the antibody composition is likely subjected to one or more virus removal steps. A virus is "removed" when it is either inactivated or physically removed from the composition (or both). In some embodiments of the present invention, a virus removal step is carried out after the capture process and before polishing and/or after polishing and before UF/DF. Typically a virus inactivation step is carried out after capture and before polishing. A virus physical removal step is typically performed after polishing and before UF/DF.

When referring to the inactivation of viruses, the viruses may remain in the final product, but in a non-infective form. The virus inactivation step may comprise a pH inactivation step and/or a chemical inactivation step. The pH inactivation step can include adjusting the pH of the composition to a pH of about 5.0 or less, often about 4.0 or less and typically in the range of about 1.5 to about 4.5, more typically about 2.0 to about 4.0. The pH inactivation step can include incubating the composition at one or more pH values within the above range for various lengths of time sufficient for viral removal (e.g., viral inactivation) to occur, e.g., 1 minute to 2 hours and typically 45 minutes to 75 minutes. The chemical inactivation step can include treatment with solvents or detergents, irradiation, and/or brief exposures to high temperatures sufficient to inactivate a virus. These methods of viral inactivation are known to those of skill in the art, and one of skill in the art can select an appropriate treatment condition.

When the virus removal step comprises the physical removal of the virus from the composition, typically filtering is involved. Specifically, nanofiltration comprises passing the composition through a matrix having a pore size of, e.g., less than 75 nm such as less than 50 nm and even less than 15 nm, to separate the virus from the antibody. Various nanofilters are available commercially and are known in the art.

The partially-purified antibody composition, with or without virus removal steps, can be subjected to UF/DF to form a UF/DF-purified antibody composition. UF/DF is a combined operation of ultrafiltration and diafiltration. The step removes particles, concentrates the antibody, and exchanges/modifies the aqueous or buffer composition of the antibody composition. Though well known in the art, for clarity the term "ultrafiltration" refers to the process of separating impurities from the antibody by passing the composition through one or more semi-permeable filter(s) (or membrane or medium) of a specified pore size diameter, wherein larger molecules (generally >103-106 Da) are retained on the filter, while water and lower molecular weight molecules pass through the filter. These lower molecular weight molecules could be media components, antibody fragments, and/or other contaminants (impurities) such as, e.g., lipopolysaccharides. Typically the antibody of the present invention is substantially in the retentate stream, while impurities are substantially in the permeate stream. The term "permeate stream" when referring to filtration refers to the fraction of the composition that passes through the filter pores during filtration. The term "retentate stream" when referring to filtration refers to the fraction of the composition that remains on the filter or that does not pass through the filter pores during filtration. This process also concentrates the antibody composition.

Suitable types of UF/DF apparatuses are known to those in the art and can be selected based on various factors, e.g., the molecular weight of the antibody to be filtered, the amount and size of the components of the composition to be filtered, the volume of the composition to be filtered, and the cell density and viability of the composition to be filtered. In some embodiments, filters, such as membrane ultrafilters, plate ultrafilters, cartridge ultrafilters, bag ultrafilters, or vacuum ultrafilters can be used. Commercially available ultrafilters that can be employed are manufactured by various vendors such as Millipore Corporation (Billerica, Mass.), Pall Corporation (East Hills, N.Y.), GE Healthcare Sciences (Piscataway, N.J.), and Sartorius Corporation (Goettingen, Germany).

The diafiltration serves to ready the antibody composition for its end use, such as storage, lyophilization, parenteral formulation, etc. The buffer system is typically exchanged and/or modified by adding/removing/replacing buffering agents and/or their concentration. Additional additives can be introduced, for example to adjust pH, tonicity, solubility, and/or stability. Stability can refer to stabilizing the antibody composition in the liquid state or to protecting the antibody during lyophilization or reconstitution. For example, in a trastuzumab composition, trehalose can be added as a stabilizer.

If the end use of the antibody composition is a parenteral formulation, it is possible to add some or all of the desired formulation excipients via the diafiltration step. These excipients can include phosphate buffer (e.g. sodium phosphate solutions), saline (e.g. 0.8%), Ringer's dextrose, dextrose and sodium chloride, lactated Ringer's, electrolytes, surfactants (polysorbate), stabilizers, and preservatives such as antimicrobials or antioxidants.

The diafiltration need not place the composition in final pharmaceutical form nor provide every excipient. Additional excipients or complete changing of the composition can be carried out after UF/DF or the subsequent AEX treatment step. Nevertheless, the UF/DF step generally places the antibody composition in near-final pharmaceutical form and thus one or more of the above additives may be introduced during UF/DF into the UF/DF-purified antibody composition.

The UF/DF-purified antibody composition is subjected to AEX as described above to reduce one or more impurities such as HCP and form a pharmaceutically pure antibody composition. For efficiency reasons, the AEX treatment usually directly follows the UF/DF step. It is possible, however, for intervening steps to occur. Such steps could include an additional UF step or a virus removal step. In preferred embodiments, no other chromatographic purification step is interposed between the UF/DF step and the AEX step. This preference does not exclude multiple AEX steps.

After the AEX step of the present invention, the antibody composition can be further modified for its end use. While additional steps after the AEX step are possible, typically no further chromatographic purification step is performed. Virus removal steps may be performed as well as composition modification. Before filling into bulk or vials, any of the following steps may be performed: (a) adding an excipient to said pharmaceutically-pure antibody composition; (b) concentrating said pharmaceutically-pure antibody composition; (c) diluting said pharmaceutically-pure antibody composition; (d) adjusting the pH of said pharmaceutically-pure antibody composition; and/or (e) sterile filtering said pharmaceutically-pure antibody. With or without additional steps, the antibody composition may be ready for bulk fill or for dispensing into vials as a parenteral formulation. Alternatively, the composition may be lyophilized for storage and later reconstitution.

In embodiments, the pharmaceutically-pure antibody composition having been subjected to AEX according to the present invention has an antibody concentration of 5 to 150 mg/ml, such as 15 to 50 mg/ml and 20-25 mg/ml.

The pharmaceutical compositions containing the antibody made by the method of the invention can comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, polyethylene-polyoxypropylene-block polymers, and polyethylene glycol. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral formulations may be a single bolus dose, an infusion or a loading bolus dose followed with a maintenance dose.

When isolating antibodies, in some embodiments large volumes of a composition can be present, e.g., during commercial manufacturing processes. Cell cultures expressing the antibodies to be isolated can be grown in a vessel appropriately sized for large-scale manufacture such as a bioreactor. Large volumes present several challenges for isolating processes. For example, the effect that a small change in flow rate through a filter has on the recovery of an isolated antibody is amplified when large volumes are used. Likewise, when using large volumes, the effect that an increase in cell density in the original composition has on product recovery is also amplified. Thus, the use of large volumes of a composition presents unique problems that are amplified and have greater ramifications relative to the use of smaller volumes. Accordingly, in some embodiments the present invention is directed to a method of isolating an antibody present in a large volume of a composition. The term "large volume" refers to volumes associated with the commercial and/or industrial production of an antibody. In some embodiments, the term "large volume" refers to 10 to 2,000 liters, 20 to 1,000 liters or 50 to 500 liters. In some embodiments, the term "large volume" refers to at least 500 liters, at least 750 liters, at least 1,000 liters, at least 1,250 liters, at least 1,500 liters, at least 2,000 liters, at least 5,000 liters or at least 10,000 liters.

In some embodiments, the invention is directed to an antibody made by any of the methods described herein.

In some embodiments, the antibody or composition comprising the antibody made by any of the methods described herein is pharmaceutically acceptable. "Pharmaceutically acceptable" refers to an antibody or composition that is, within the scope of sound medical judgment, suitable for contact with the tissues of human beings and animals without excessive toxicity or other complications commensurate with a reasonable benefit/risk ratio.

In some embodiments, the antibody isolated by the methods of the present invention can be used in the treatment of a subject. As used herein, "subject" refers to any animal classified as a mammal, including humans and non-humans, such as, but not limited to, domestic and farm animals, zoo animals, sports animals, and pets. In some embodiments, subject refers to a human.

The terms "treat" and "treatment" refer to both therapeutic treatment and prophylactic, maintenance, or preventative measures, wherein the object is to prevent or alleviate (lessen) an undesired physiological condition, disorder or disease, or obtain beneficial or desired clinical results.

The route of administration of the isolated antibody product of the method of the present invention can be via, for example, oral, parenteral, inhalation or topical modes of administration.

The invention is further illustrated by the following non-limiting examples.

EXAMPLES

Example 1

Conventional Purification

The following procedure was used to purify four runs. A composition comprising trastuzumab produced from CHO cells was subjected to capture on a Protein A column, virus inactivation, polishing using AEX followed by CEX, virus filtered, and then subjected to UF/DF. The steps were performed as follows:

The Protein A step (MabSelect SuRe, GE Healthcare) started with sanitization of a column with 0.1 M NaOH for 15 minutes, followed by a rinse with Milli Q purified water (MQ). The column was then equilibrated with PBS at pH 7.4. The harvest was loaded onto the column at a ratio of ≤25 mg trastuzumab per ml MabSelectSure. The column was then washed with equilibration buffer, followed by a wash with 25 mM NaAc pH 5.0. Antibody was then eluted with 25 mM Acetate pH 3.0.

Virus inactivation followed. The pH of the Protein A elution pool was brought to pH 3.5 with 0.1 M HCl and held at this pH for 60-75 minutes. The pH was raised again to pH 4.5 with 0.1 M NaOH, followed by sterile filtration with a 0.22 µm filter.

Anion exchange chromatography followed. An anion exchange membrane (Mustang Q filter, Pall) was preflushed with MQ, followed by a sanitization with 1.0 M NaOH for 5 membrane volumes (MV). After neutralization with 25 mM H3PO4+1 M NaCl the filter was equilibrated with 25 mM NaAc+10 mM NaCl at pH 4.5. The filter was loaded with maximally (≤) 3.0 g (ml MV)-1 antibody from the virus inactivation step above. The antibody flowed through the filter while contaminants like residual CHO proteins and DNA bound to the filter. The filter was flushed with 25 mM NaAc+10 mM NaCl pH 4.5 and the eluted product was filtered through a 0.22 μm sterile filter.

Cationic exchange chromatography followed. The cationic exchange chromatography column (Poros HS 50 column; Applied Biosystems) was sanitized with 0.5 M NaOH and rinsed with MQ. Equilibration was done with 25 mM NaAc pH 4.5+10 mM NaCl. The anion exchange chromatographic process purified antibody bulk was loaded with a concentration of 10-20 g antibody/mL resin. The column was then washed with equilibration buffer, followed by a wash with 25 mM NaAc pH 4.5+200 mM NaCl. The antibody product was then eluted using a gradient from 25 mM NaAc pH 4.5+200 mM NaCl to 25 mM NaAc pH 4.5+290 mM NaCl in 3 column volumes. Elution was continued with 25 mM NaAc pH 4.5+290 mM NaCl.

Virus filtration followed. The cationic exchange chromatography antibody product was virus filtered using a Viresolve Pro membrane (Millipore) using a pressurized filtration system, according to the instructions of the suppliers. The Viresolve pro device was preflushed with MQ and equilibrated with 25 mM NaAc+290 mM NaCl pH 4.5. After applying the CEX bulk with a load of <565 g m-2 (Planova), <2 kg m-2 (Viresolve Pro) the filter was flushed with 25 mM NaAc+290 mM NaCl pH 4.5. After the filtration stopped, the antibody product was virus filtered using a 0.22 μm filtered.

Ultrafiltration/Diafiltration (UF/DF) were performed using a Biomax 50KD (Run 1) or 30 KD (Runs 2-4) UFDF filter (Millipore) with a molecular weight cut-off of 30 kDa. The filter was preflushed with MQ, sanitized with 0.1 M NaOH. followed by a rinse with MQ to remove the NaOH. The filter was then equilibrated with 25 mM Acetetate pH 4.5+290 mM NaCl. The virus filtered antibody product was subsequently loaded on the filter using a load of ≤730 g antibody/m2 membrane. After concentration to 25-35 mg/ml, the buffer of the antibody product was exchanged to 50 mM Trehalose+4.2 mM Histidine pH 6.0. 10 Diafiltration volumes were used to exchange the buffer.

The final product for each run was tested for content, product-related impurities (dimers, aggregates), and process-related impurities (HCPs, res ProtA, resDNA). A summary of those results is in Table 1 (LOQ means limit of quantification).

TABLE 1

A summary of results obtained from 4 runs

| Run | Trastuzumab Content (mg/ml) | Dimers/ Aggregates (%) | HCP[1] ppm | HCP[2] ppm | res Prot A ppm |
|---|---|---|---|---|---|
| Run 1 | 20.3 | 0.34/0 | 3.3 | 43.7 | <LOQ |
| Run 2 | 19.9 | 0.15/0 | 4.2 | 80.8 | 2.0 |
| Run 3 | 19.9 | 0.37/0 | 7.4 | 62.9 | <LOQ |
| Run 4 | 19.5 | 0.25/0 | 6.0 | 24.3 | <LOQ |

[1]For these values the F015 CHO kit (Cygnus) was used.
[2]For these values the F550 CHO kit (Cygnus) was used.

The inventors note that using an older kit, the F015 CHO kit (Cygnus), the host cell protein (HCP) values appeared to be less than 10 ppm. However, when the test was repeated using the newer, more sensitive F550 CHO kit (Cygnus), it was discovered that the host cell proteins were actually present at unsuitably higher level than previously noted. It was desired by the inventors to lower the HCP levels to less than 10 ppm.

For product related impurities (like dimers, aggregates of FTMB), all four samples had suitably low levels of product related impurities (Table 1). All product or process related impurities (except the CHO proteins) were removed to the desired threshold levels.

Example 2

Purification with an Anion Exchange Chromatography Process after the Final Ultrafiltration Process A composition comprising trastuzumab produced from CHO cells was purified as described in Example 1, with the following differences. For Run 5, the Protein A step was modified to include a 1M sodium chloride wash, the virus filtration step was eliminated, the UF/DF step used a vivaspin device, and 1000 diafiltration volumes were used to exchange the buffer. For Run 6, the Protein A step was modified to include a 1M sodium chloride wash, the virus filtration step used a Plenova 15 N filter (Asahi Kasei), and the UF/DF step used an Ultracel 30 KD filter. Additionally, the pre-UF/DF anion exchange chromatography (AEX) step of Example 1 was eliminated and the following AEX step was added after the UF/DF step.

AEX on the Concentrated and Diafiltrated Material:

For anion exchange chromatography a Mustang Q filter (Pall) was used. The membrane was preflushed with MQ which was followed by a sanitization of 1.0 M NaOH for 5 membrane volumes (MV). After neutralization with 25 mM H3PO4+1 M NaCl followed by a MQ flush, the filter was equilibrated with 50 mM Trehalose+4.2 mM Histidine pH 6.0. For Run 5, the filter was loaded with 0.36 g trastuzumab (ml MV)-1; For Run 6, the filter was loaded with maximally (≤) 3.0 g trastuzumab (ml MV)-1. Antibody flowed through the filter while contaminants like residual CHO proteins and DNA bind to the filter. The filter was flushed with 50 mM Trehalose+4.2 mM Histidine pH 6.0 and the collected flow through was filtered through a 0.22 μm sterile filter.

Final samples from two separate runs of were tested for content, product related impurities (dimers, aggregates), and process related impurities (HCPs, res ProtA, resDNA). A summary of those results is provided in Table 2.

TABLE 2

A summary of results obtained from 2 runs

| Run | Trastuzumab Content (mg/ml) | Dimers/ Aggregates (%) | HCP[1] ppm | res Prot A ppm | DNA ppb |
|---|---|---|---|---|---|
| 5 | 7.90 | 0.5/0 | <1 | n/d | <10 |
| 6 | 23.4 | nd | <0.65 | <0.04 | <0.07 |

[1]For these values the F550 CHO kit (Cygnus) was used.
nd: not determined.

The host cell proteins levels were below the desired HCP levels (less than 10 ppm) using the newer, more sensitive F550 CHO kit (Cygnus) for detection. Both samples had had suitably low levels of process and product related impurities (e.g., dimers, aggregates of trastuzamab). This result demonstrates that the overall purity is improved using the same number of steps by re-locating the AEX step to after the final UF/DF step.

Example 3

Purification with an Anion Exchange Chromatography Process Before and after the Final Ultrafiltration Process A composition comprising trastuzumab produced from CHO cells was purified as described in Example 1, with the following differences. For runs 7-10, the virus filtration step used a Plenova 15 N filter (Asahi Kasei), and the UF/DF step used an Ultracel 30 KD filter. Additionally, a further AEX step was performed after the UF/DF step, and the further AEX step was performed as described for Run 2 in Example 2.

Final samples from four separate runs were tested for content, product related impurities (dimers, aggregates), and process related impurities (HCPs, res ProtA, resDNA). A summary of those results is in Table 3.

TABLE 3

A summary of results obtained from 4 runs

| Run | Trastuzumab Content (mg/ml) | Dimers/ Aggregates (%) | HCP[2] ppm | res Prot A ppm | DNA ppb |
|---|---|---|---|---|---|
| 7 | 23.3 | 0.31/0.03 | 7.47 | <0.3 | nd |
| 8 | 21 | monomers: 99.4 | <0.47 | <0.83 | <1.0 |
| 9 | 24 | monomers: 99.5 | <0.50 | <0.81 | <1.0 |
| 10 | 23 | monomers: 97.4 | <1.4 | <0.88 | <1.0 |

[2]For these values the F550 CHO kit (Cygnus) was used.
nd: not determined

The host cell proteins levels (from the process having two anion exchange chromatography process: one before and one after the UF/DF step) were below the desired HCP levels (less than 10 ppm) using the newer, more sensitive F550 CHO kit (*Cygnus*) for detection for the four runs which were tested. Process and product related impurities were also suitably low.

These examples demonstrate that increased purity of antibodies (e.g., decreased host cell protein concentration) can be achieved by performing an anion exchange chromatography process after the final UF/DF process.

CONCLUSION

All of the various embodiments or options described herein can be combined in any and all variations. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

The invention claimed is:

1. A method of purifying an antibody composition, wherein the antibody is produced in eukaryotic cells, which comprises subjecting a UF/DF-purified antibody composition to anion exchange chromatography (AEX) to form a pharmaceutically-pure antibody composition, wherein said anion exchange chromatography is the last chromatographic purification step and is performed directly after the final UF/DF step.

2. The method of claim 1, wherein said UF/DF-purified antibody composition has an antibody concentration of at least 1 mg/ml.

3. The method of claim 2, wherein said UF/DF-purified antibody composition has an antibody concentration of at least 10 mg/ml.

4. The method of claim 3, wherein said UF/DF-purified antibody composition has an antibody concentration of not greater than 250 mg/ml.

5. The method of claim 4, wherein said UF/DF-purified antibody composition has an antibody concentration of 20 to 50 mg/ml.

6. The method of claim 1, which further comprises filling said pharmaceutically-pure antibody composition into vials.

7. The method according to claim 6, which further comprises aseptically filtering said pharmaceutically-pure antibody composition prior to said filling step.

8. The method according to claim 7, which further comprises at least one of the following steps prior to said filling step: (a) adding an excipient to said pharmaceutically-pure antibody composition; (b) concentrating said pharmaceutically-pure antibody composition; (c) diluting said pharmaceutically-pure antibody composition; and/or (d) adjusting the pH of said pharmaceutically-pure antibody composition.

9. The method of claim 1, wherein said UF/DF-purified antibody composition is obtained by subjecting a partially-purified antibody composition to UF/DF.

10. The method of claim 9, wherein an antibody cell culture harvest is subjected to an antibody capture step and optionally at least one polishing step to form said partially-purified antibody composition.

11. The method of claim 10, wherein said capture step utilizes affinity chromatography.

12. The method of claim 11, wherein said affinity chromatography is Protein A chromatography.

13. The method of claim 10, wherein said capture step utilizes cation exchange chromatography (CEX), hydrophobic charge induction chromatography (HCIC), or mixed mode chromatography.

14. The method of claim 10, wherein at least one polishing step is carried out after said capture step.

15. The method according to claim 14, wherein said at least one polishing step is selected from the group consisting of ion exchange chromatography (IEX), hydrophobic interaction chromatography (HIC), and hydroxyapatite chromatography.

16. The method of claim 1, wherein said antibody is trastuzumab or pertuzumab.

17. The method of claim 1, wherein said antibody was produced in CHO cells.

18. A method of purifying an antibody composition, which comprises:
   subjecting an antibody eukaryotic cell culture harvest to affinity chromatography to capture a crude antibody composition;
   subjecting the crude antibody composition to at least one polishing step to form a partially-purified antibody composition;
   subjecting the partially-purified antibody composition to a UF/DF step to form a UF/DF-purified antibody composition; and
   subjecting the UF/DF-purified antibody composition to anion exchange chromatography (AEX) to form a pharmaceutically-pure antibody composition,
   wherein said anion exchange chromatography is the last chromatographic purification step and is performed directly after the final UF/DF step.

19. The method of claim 18, wherein said affinity chromatography is Protein A chromatography.

20. The method of claim 18, which further comprises subjecting said pharmaceutically-pure antibody composition to a virus removal step.

21. The method of claim 20, wherein said virus removal step is nanofiltration.

22. The method of claim 18, wherein said at least one polishing step comprises subjecting said crude antibody composition to at least one ionic exchange chromatography (IEX) step.

* * * * *